(12) United States Patent
Nakabayashi (10) Patent No.: US 10,398,408 B2
(45) Date of Patent: Sep. 3, 2019

(54) EXAMINATION PORTION INFORMATION OBTAINING APPARATUS

(71) Applicant: CANON KABUSHIKI KAISHA, Tokyo (JP)

(72) Inventor: Takaaki Nakabayashi, Kawasaki (JP)

(73) Assignee: Canon Kabushiki Kaisha, Tokyo (JP)

(*) Notice: Subject to any disclaimer, the term of this patent is extended or adjusted under 35 U.S.C. 154(b) by 760 days.

(21) Appl. No.: 14/527,569

(22) Filed: Oct. 29, 2014

(65) Prior Publication Data

US 2015/0119714 A1  Apr. 30, 2015

(30) Foreign Application Priority Data

Oct. 31, 2013  (JP) .................................. 2013-227238

(51) Int. Cl.

| | | |
|---|---|---|
| *A61B 5/05* | (2006.01) | |
| *A61B 8/00* | (2006.01) | |
| *A61B 5/00* | (2006.01) | |
| A61B 8/08 | (2006.01) | |
| A61B 5/11 | (2006.01) | |

(52) U.S. Cl.
CPC ............ *A61B 8/406* (2013.01); *A61B 5/0095* (2013.01); *A61B 5/6844* (2013.01); *A61B 5/708* (2013.01); *A61B 5/0091* (2013.01); *A61B 5/1128* (2013.01); *A61B 8/085* (2013.01); *A61B 8/0825* (2013.01); *A61B 8/4254* (2013.01); *A61B 8/4281* (2013.01)

(58) Field of Classification Search
None
See application file for complete search history.

(56) References Cited

U.S. PATENT DOCUMENTS

| 4,541,436 A | 9/1985 | Hassler | |
|---|---|---|---|
| 2005/0143638 A1* | 6/2005 | Johnson | A61B 5/4312 600/407 |
| 2007/0237306 A1 | 10/2007 | Jones | |
| 2007/0239020 A1* | 10/2007 | Iinuma | A61B 8/0825 600/459 |
| 2011/0306865 A1* | 12/2011 | Thornton | A61B 5/0059 600/407 |
| 2013/0312526 A1* | 11/2013 | Oishi | A61B 5/0095 73/620 |

FOREIGN PATENT DOCUMENTS

| CN | 103354731 A | 10/2013 | |
|---|---|---|---|
| CN | 103356233 A | 10/2013 | |
| JP | 2007-216003 A | 8/2007 | |
| JP | 2012-179348 A | 9/2012 | |
| WO | 20101030817 A1 | 3/2010 | |
| WO | 2012108172 A1 | 8/2012 | |
| WO | WO 2012108172 A1 * | 8/2012 | ........... A61B 5/0095 |

* cited by examiner

*Primary Examiner* — Jonathan Cwern
(74) *Attorney, Agent, or Firm* — Canon U.S.A. Inc., IP Division (57) ABSTRACT

An examination portion information obtaining apparatus includes an opening to which a portion to be examined of the examinee is inserted, a cup-shaped maintaining member which accommodates at least part of the portion to be examined inserted through the opening, an acoustic wave detector which receives acoustic waves from the portion to be examined, and a movement mechanism which moves the maintaining member relative to the portion to be examined inserted through the opening.

18 Claims, 11 Drawing Sheets

EXAMINATION PORTION INFORMATION OBTAINING APPARATUS

BACKGROUND OF THE INVENTION

Field of the Invention

The present invention relates to examination portion information obtaining apparatuses, and particularly relates to an examination portion information obtaining apparatus utilizing a photoacoustic effect.

Description of the Related Art

A technique of detecting formation of a new blood vessel and oxygen metabolism of hemoglobin caused by growth of a tumor from an optical absorption property of the hemoglobin included in blood using light having a wavelength of approximately 600 to 1500 nm which has an excellent transmission property relative to a biological tissue so that results of the detection is used for diagnosis of the tumor has been used. Examples of the technique include a technique using a photoacoustic effect.

The photoacoustic effect is a phenomenon in which, when pulsed light of approximately nanosecond is irradiated on a substance, the substance absorbs optical energy due to an optical absorption property and is instantaneously expanded so that an elastic wave is generated. The elastic wave is detected by an ultrasonic probe so that a reception signal is obtained. When the reception signal is mathematically subjected to an analysis process, an absorption property in a living body may be represented by an image in accordance with sound pressure distribution of the elastic wave generated due to the photoacoustic effect. The hemoglobin is preferably used in a method for measuring the new blood vessel and the oxygen metabolism described above since the hemoglobin has higher absorptivity of near infrared light when compared with water, fat, and protein which constitute a body tissue. Clinical research to be applied to diagnosis of breast cancer and the like has been positively conducted using such a photoacoustic effect.

As a photoacoustic apparatus, International Publication Pamphlet No. WO2010/030817 discloses an apparatus including an acoustic wave detector which has a hemispherical shape and which includes a plurality of acoustic elements arranged thereon and a container having a cup shape to which a portion to be examined of a subject is to be inserted. This apparatus includes a photoacoustic detector having a hemispherical shape below the container and a light irradiation unit which irradiates light to a portion to be examined below the acoustic wave detector having the hemispherical shape. With this apparatus configuration, improvement of resolution of an information image obtained by receiving acoustic waves from the portion to be examined in a plurality of directions is realized.

When the apparatus according to International Publication Pamphlet No. WO2010/030817 is employed in an examination portion information obtaining apparatus for breasts, an examinee inserts a breast to the cup after positioning the breast in the cup-shaped container since the cup-shaped container is fixed to the apparatus.

However, when the breast is inserted in a state in which a position of the breast is shifted from the cup-shaped container, the examinee is requested to insert the breast in the cup-shaped container again by changing a posture so that a position of the cup-shaped container and a position of the breast coincide with each other. This operation is repeatedly performed until positioning between the cup-shaped container and the breast is within an allowable range. Accordingly, there arises a problem in that the examinee is forced to bear the burden. Furthermore, there arises a problem in that, when image information is obtained in a state in which the positioning between the cup-shaped container and the breast is out of the allowable range, reliability of the image information is degraded. Specifically, a measurement target portion in the breast may be located out of an imaging range.

SUMMARY OF THE INVENTION

The present invention provides an examination portion information obtaining apparatus capable of reducing a burden of an examinee and obtaining a highly-reliable image.

According to an embodiment of the present invention, there is provided an examination portion information obtaining apparatus including a maintaining member configured to accommodate at least part of a portion to be examined of an examinee, an acoustic wave detector configured to receive acoustic waves from the portion to be examined, and a movement mechanism configured to move the maintaining member.

Further features of the present invention will become apparent from the following description of exemplary embodiments with reference to the attached drawings.

DESCRIPTION OF THE EMBODIMENTS

Embodiments of the present invention will be described with reference to the accompanying drawings. The present invention is not limited to configurations described below without departing from the scope of the invention.

In the embodiments, an example of an apparatus which irradiates light to a portion to be examined and receives an acoustic wave (typically, an ultrasonic wave) generated from the portion to be examined using a detector so as to obtain examination portion information will be described. The examination portion information to be obtained is feature information obtained by reflecting initial sound pressure distribution of an acoustic wave generated by light irradiation, optical energy absorption density distribution derived from the initial sound pressure distribution, absorption coefficient distribution, and distribution of concentration of a substance constituting a tissue. Examples of the distribution of concentration of a substance include oxygen saturation distribution, distribution of concentration of oxygenated hemoglobin, and distribution of concentration of reduced hemoglobin. Furthermore, the examination portion information may be obtained not only as numerical data but also as information on distribution in positions included in the portion to be examined. Specifically, the distribution information such as the absorption coefficient distribution and oxygen saturation distribution may be obtained as image data.

Note that an apparatus employing an ultrasonic echo technique of transmitting an ultrasonic wave to a portion to be examined and receiving a reflected wave reflected by an inside of the portion to be examined so that examination portion information is obtained may be used as the examination portion information obtaining apparatus of the embodiments. When the apparatus utilizing the ultrasonic wave echo technique is used, examination portion information to be obtained is feature information obtained by reflecting a difference between acoustic impedances of a tissue included in the portion to be examined.

Figure 1:
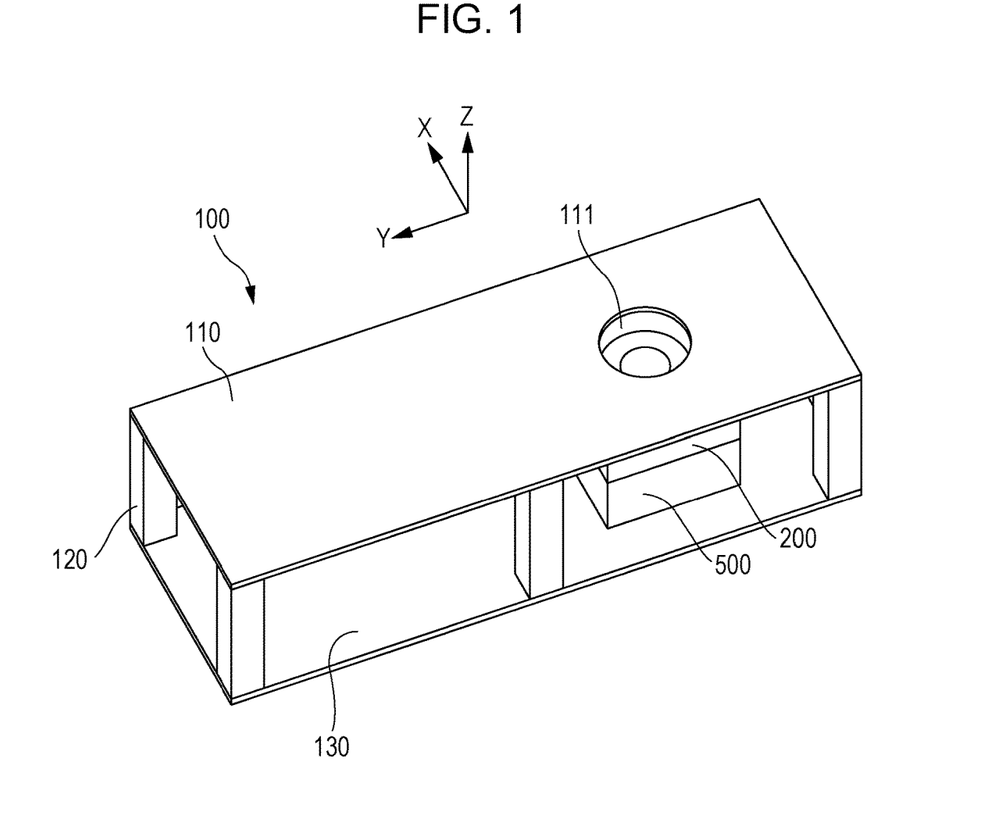
FIG. 1 is a perspective view illustrating an examination portion information obtaining apparatus according to a first embodiment.
Figure 2:
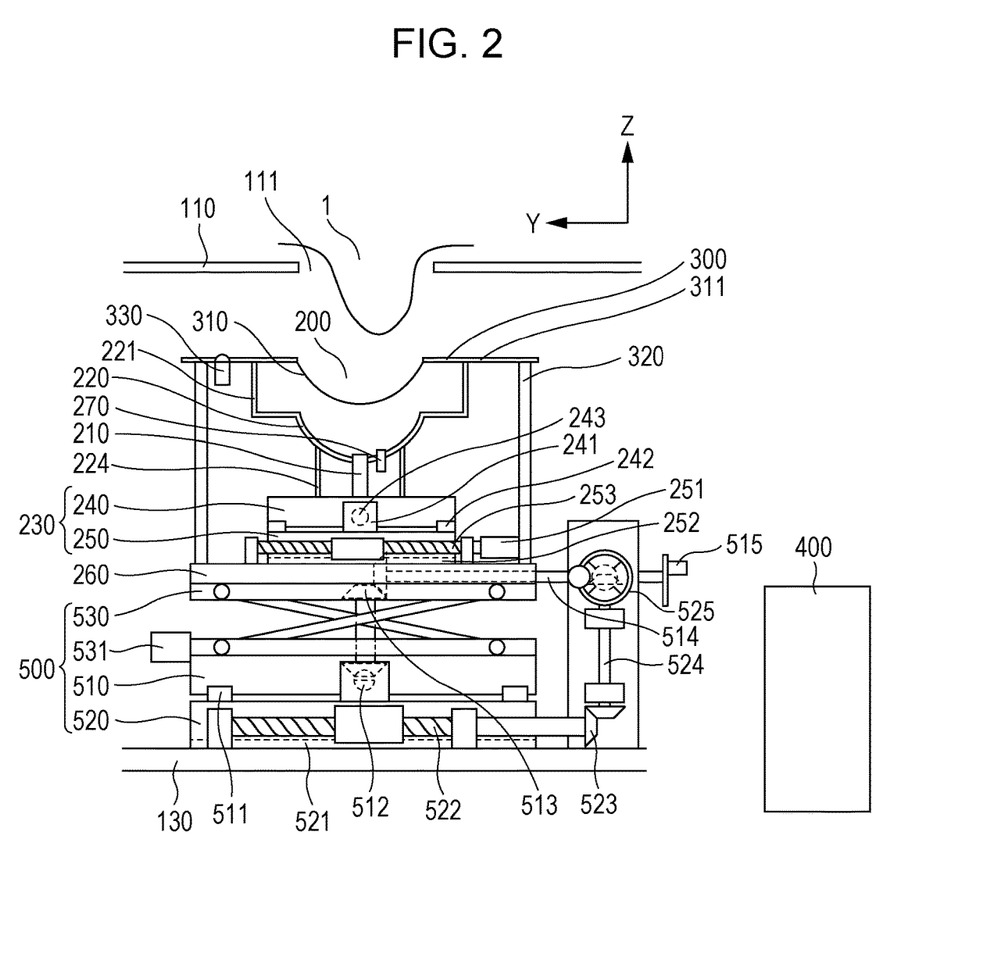
FIG. 2 is a side view illustrating an internal configuration of the examination portion information obtaining apparatus according to the first embodiment.

Next, units according to this embodiments will be described with reference to FIGS. 1, 2, 3A, and 3B. FIG. 1 is a perspective view illustrating an examination portion information obtaining apparatus. FIG. 2 is a side view illustrating an internal configuration of the examination portion information obtaining apparatus.

Bed Unit 100

An examinee lies on a bed unit 100 in a prone posture. The bed unit 100 includes a bed 110 which is a supporting member for maintaining a posture of the examinee, bed legs 120 for supporting the bed 110, and a base 130. The bed 110 (a subject supporting member) has an opening 111 for inserting a breast 1 which is a portion to be examined of the subject. The breast 1 inserted through the opening 111 sags downward due to gravity.

Measurement Unit 200

A measurement unit 200 which is an acoustic wave detection unit irradiates light to the breast 1 and has a detector which receives an ultrasonic wave generated by the breast 1. As illustrated in FIG. 2, the measurement unit 200 includes a light irradiation unit 210 which irradiates light to the breast 1, an ultrasonic wave detector 220 which has a hemispherical shape and which receives an ultrasonic wave from the breast 1, a scanning stage 230 which causes the light irradiation unit 210 and the ultrasonic wave detector 220 to perform 2D scanning, and a measurement unit base 260.

Figure 3A:
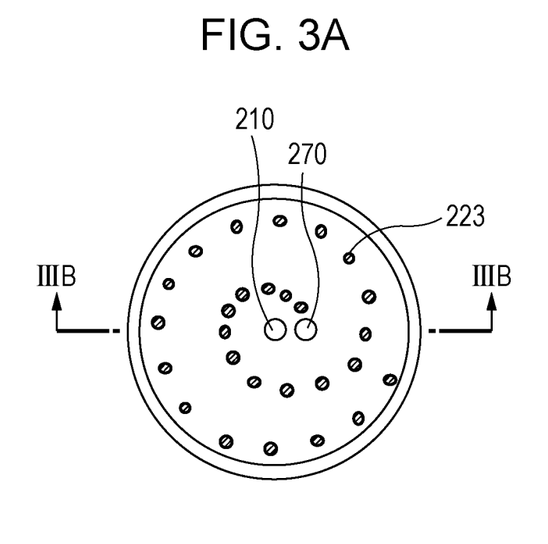
FIG. 3A is a diagram schematically illustrating an acoustic wave detector according to the first embodiment.
Figure 3B:
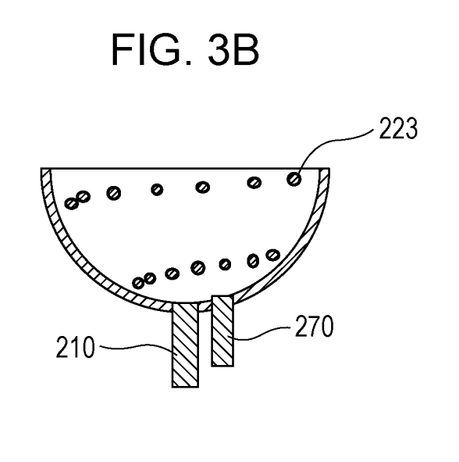
FIG. 3B is a sectional view illustrating the acoustic wave detector taken along a line IIIB.

FIG. 3A is a diagram schematically illustrating the ultrasonic wave detector 220 and FIG. 3B is a sectional view illustrating the ultrasonic wave detector 220 taken along a line IIIB. The ultrasonic wave detector 220 is disposed such that an opening of the ultrasonic wave detector 220 faces a cup 310 described below so that a center of curvature of a hemispherical shape is located in the inside of the cup 310. The shape may be a 1/n spherical shape (n is an integer) or a shape which approximates a hemispherical shape or a 1/n spherical shape by connecting a plurality of plane surfaces with one another. Furthermore, a plurality of acoustic detection elements 223 are disposed on an inner surface of the ultrasonic wave detector 220. The acoustic detection elements 223 are spirally disposed around the center of the hemispherical ultrasonic wave detector 220 at regular intervals. A directivity direction of the acoustic detection elements 223 is fixed toward the center of the curvature of the hemisphere. Since the acoustic detection elements 223 are disposed as described above, ultrasonic waves generated from the portion to be examined may be obtained at wider angle and directional sensitivity of the acoustic detection elements 223 may be concentrated on a narrow region in the cup 310, and accordingly, highly-sensitive detection may be performed. As a result, image reconstruction may be performed at high sensitivity using obtained signals output from the acoustic detection elements 223.

The light irradiation unit 210 and a camera 270 which will be described hereinafter are disposed on a lower portion of the ultrasonic wave detector 220. The acoustic detection elements 223 receive photoacoustic waves and convert the photoacoustic waves into electric signals. Examples of members constituting the acoustic detection elements 223 include piezoelectric ceramic material such as PZT (lead zirconate titanate) or polymer piezoelectric film material such as PVDF (polyvinylidene fluoride). Alternatively, elements other than piezoelectric elements may be used. For example, electrostatic capacitance elements such as CMUT (Capacitive Micro-machined Ultrasonic Transducers) may be used.

The light irradiation unit 210 is disposed such that light is irradiated toward the breast 1 from a lower portion of the ultrasonic wave detector 220. The light is guided to the light irradiation unit 210 from a light source, not illustrated, through an optical system. The light source emits pulsed light of a nano-second order having a specific wavelength. As the wavelength of the light emitted from the light source, a wavelength corresponding to optical absorption property such as waver, fat, protein, oxygenate hemoglobin, or reduced hemoglobin which constitutes a body tissue is selected. For example, a wavelength in a range from 600 to 1500 nm is appropriately used in which light is easily transmitted since absorption of water which is a main component of a body inner tissue is small and light absorption property of fat, oxygenate hemoglobin, and reduced hemoglobin is distinctive. As concrete examples of the light source, a semiconductor laser and a wavelength tunable laser which generate different wavelengths may be used. As the optical system, a multi-joint arm which is configured to follow scanning performed by the ultrasonic wave detector 220 and which allows transmission of light in a space using an optical fiber or a mirror may be employed.

As illustrated in FIG. 2, the ultrasonic wave detector 220 is configured such that the ultrasonic wave detector 220 and a matching container 221 which maintains matching liquid used for acoustic matching with a cup 310 (a cup-shaped container) which is a supporting member of the breast 1 which will be described below are integrated. The matching liquid is supplied to the ultrasonic wave detector 220 and the matching container 221 and discharged from the ultrasonic wave detector 220 and the matching container 221 by a pump and a matching liquid circulating system, not illustrated. As the matching liquid, oil or water which has a high transmission property and a low attenuation property relative to a photoacoustic wave is preferably used.

The scanning stage 230 is a movement mechanism which moves the ultrasonic wave detector 220 relative to the cup 310 which is the supporting member. The scanning stage 230 includes an X scanning stage 240 which causes the light irradiation unit 210 and the ultrasonic wave detector 220 to perform scanning in an X direction and a Y scanning stage 250 which causes the light irradiation unit 210 and the ultrasonic wave detector 220 to perform scanning in a Y direction. Here, the X direction is orthogonal to a body axis of the examinee in a state in which the examinee is supported in a prone posture. The Y direction is parallel to the body axis of the examinee in the same state. A Z direction corresponds to a gravity direction, that is, a direction in which the breast 1 sags or a direction in which the breast 1 is inserted and maintained. The X scanning stage 240 is disposed on the Y scanning stage 250, and the ultrasonic wave detector 220 is fixed to the X scanning stage 240 using the poles 224. The X scanning stage 240 and the Y scanning stage 250 are controlled by an instruction issued by a calculation unit 400 described below using motors 241 and 251, linear guide 242 and 252, and ball screws 243 and 253, respectively. With this configuration, the ultrasonic wave detector 220 may perform 2D scanning in the X and Y directions (scanning in a plane perpendicular to a direction in which the breast 1 is inserted (the breast 1 sags)). The mechanism of the scanning stage 230 is not limited to the mechanism described above, and any mechanism including a link mechanism, a gear mechanism, and a hydraulic mechanism may be used as long as the ultrasonic wave detector 220 is driven to perform scanning. Furthermore, the scanning may be performed using a rotation mechanism instead of a linear driving using a linear guide. Furthermore, a Z scanning stage which causes the ultrasonic wave detector 220 to perform scanning in the Z direction which is perpendicular to the X and Y directions may be provided.

Each of the X scanning stage 240 and the Y scanning stage 250 has an origin sensor and a linear encoder. Accordingly, a position of the ultrasonic wave detector 220 relative to the measurement unit 200 may be detected.

Maintaining Unit 300

A maintaining unit 300 which maintains the breast 1 includes the cup 310 which is pressed against the breast 1 and a cup assembling member 311 used to assemble the cup 310. The cup 310 has a shape capable of accommodating at least part of the breast 1 which is the portion to be examined, and preferably has a shape corresponding to a size and a shape of the breast 1. The shape is preferably a hemispherical shape or a cylindrical shape, for example. Alternatively to the cup 310, another maintaining member with changeable shape like rubber sheet may be used. The member can have a shape capable of accommodating at least part of the breast 1 when maintains breast 1. As the cup 310, a light transmissive member which has an acoustic impedance (($1.5$ to $1.6) \times 10^5$ kg/m$^2$ sec) substantially the same as that of the breast 1 and which further has high light transmissivity (preferably 90% or more) in an apparatus utilizing a photoacoustic effect is preferably used. Examples of material of the member include polymethylpentene, PET, polycarbonate, and elastomer. The cup 310 is preferably thin so as to reduce attenuation of ultrasonic waves. More preferably, the cup 310 has a thickness of ¼ of a wavelength of an ultrasonic wave so that reflection of the ultrasonic wave is prevented and noise which is harmful to reconstruction of an image is reduced. Furthermore, when measurement is performed, a matching agent such as jelly or water is preferably injected in the cup 310 so that acoustic matching between the breast 1 and the cup 310 is attained.

Calculation Unit 400

As the calculation unit 400, a workstation or the like is typically used. Although not illustrated, control target configurations including a display apparatus such as a display, an input apparatus such as a mouse or a keyboard, acoustic wave detectors including the acoustic detection elements 223, and a motor are connected to the calculation unit 400. The calculation unit 400 performs various signal processes (including image reconfiguration) on a received ultrasonic wave and control of the entire apparatus including driving control of the various components.

Trajectory of Ultrasonic Wave Detector 220 at Measurement

A scanning trajectory of the ultrasonic wave detector 220 at a time of measurement which is moved by the scanning stage 230 will be described.

The ultrasonic wave detector 220 may perform scanning in a substantially linear manner in an XY plane. For example, the ultrasonic wave detector 220 scans in the X direction (first scanning), moves in the Y direction (first moving), scans in a direction opposite to the first scanning in the X direction (second scanning), and further moves in the Y direction (second moving) in a measurement region in the XY plane. When the process including the first scanning, the first moving, the second scanning, and the second moving is repeatedly performed, the entire measurement region is measured. The ultrasonic wave detector 220 performs the scanning and the moving such that the ultrasonic wave detector 220 does not touch the cup 310.

Furthermore, a trajectory of the ultrasonic wave detector 220 (a movement trajectory of a position of the ultrasonic wave detector 220) may be a circle trajectory in the XY plane. The circle trajectory includes not only a precise circle trajectory but also an oval trajectory.

Furthermore, the trajectory of the ultrasonic wave detector 220 may be a spiral pattern in the XY plane. The spiral trajectory represents a scanning trajectory in which a coordinate of a radial direction is increased or decreased relative to a rotation center of the trajectory. A position coordinate (x, y) at a polar coordinate of a point p on the movement trajectory of the ultrasonic wave detector 220 is represented by Equation (1) below.

$$x = r(t)\cos \Phi$$

$$y = r(t)\sin \Phi \qquad (1)$$

Here, "r(t)" denotes a coordinate (a movement radius) of the radial direction, and "Φ" denotes an angle defined by an X axis and a line extending from a point of origin to the point p. In this embodiment, the ultrasonic wave detector 220 scans such that the coordinate r(t) in the radial direction on the movement trajectory of the ultrasonic wave detector 220 changes in an increase direction or a decrease direction.

Note that the scanning stage 230 preferably moves the ultrasonic wave detector 220 such that a speed of the trajectory of the ultrasonic wave detector 220 in a normal direction is constant. In general, a timing of detection of a photoacoustic wave is determined in accordance with a recurrence frequency of pulsed light emitted from the light source. Therefore, a photoacoustic wave is detected while a speed of the trajectory of the ultrasonic wave detector 220 in the normal direction is set constant so that sampling is uniformly performed relative to a space. Furthermore, the scanning stage 230 preferably moves the ultrasonic wave detector 220 from an outer side of a movement plane taking acceleration toward the point of origin of the trajectory into consideration. Specifically, if the acceleration in an initial stage of the movement is large, shake of the entire apparatus is large, and the shake may affect the measurement. Therefore, the ultrasonic wave detector 220 is moved from an outer periphery where the acceleration toward the point of origin of the trajectory is small to an inner periphery so that the shake of the apparatus is suppressed.

Furthermore, the ultrasonic wave detector 220 may be moved by the Z scanning stage in the Z direction.

Note that the operation of the measurement unit 200 associated with the measurement and the signal processing on ultrasonic waves are performed by general techniques.

Next, an example of positioning between the cup 310 which is the maintaining member and the breast 1 which is the portion to be examined will be described.

First Embodiment

In this embodiment, as illustrated in FIG. 2, the measurement unit 200 and the maintaining unit 300 are coupled to each other through fixing members 320 in an integration manner (fixed to each other). Specifically, the measurement unit base 260 and the cup assembling member 311 are fixed to each other by the fixing members 320. An adjustment stage 500 (a maintaining unit stage) which is a movement mechanism for positioning of the maintaining unit 300 relative to the breast 1 is disposed below the measurement unit 200. The adjustment stage 500 includes an X adjustment stage 510, a Y adjustment stage 520, and a Z adjustment stage 530 which adjust the maintaining unit 300 in the X, Y, and Z direction, respectively. The Y adjustment stage 520 is mounted on the base 130, the X adjustment stage 510 is mounted on the Y adjustment stage 520, and the Z adjustment stage 530 is mounted on the X adjustment stage 510. Driving mechanisms for the X adjustment stage 510 and the Y adjustment stage 520 include linear guides 511 and 521 and ball screws 512 and 522, respectively. The ball screws 512 and 522 are connected to handles 515 and 525 operated by an operator through gears 513 and 523 and shafts 514 and 524, respectively. Accordingly, when the operator rotates the handles 515 and 525, the measurement unit 200 and the maintaining unit 300 which is integrated with the measurement unit 200 are driven in the X and Y directions. With this configuration, the bed 110 which is the member for supporting the examinee and the cup 310 which is the maintaining member are movable relative to each other. Specifically, the cup 310 is movable relative to the breast 1 inserted through the opening 111. Positions and directions of the handles 515 and 525 are not limited to those in FIG. 2, and the handles 515 and 525 are preferably operated by the operator with ease. The Z adjustment stage 530 is an X link mechanism and is driven in the Z direction when a motor 531 is driven. Driving of the motor 531 is controlled by an instruction issued by the calculation unit 400. The maintaining unit 300 includes a contacting sensor 330 which detects a position of the bed 110. When the maintaining unit 300 moves toward the bed 110 and the contacting sensor 330 detects the bed 110 when the contacting sensor 330 is brought into contact with the bed 110, driving of the Z adjustment stage 530 is stopped. Here, if a gap between the bed 110 and the cup 310 is large when information on the breast 1 is to be obtained, a distance between the cup 310 or the cup assembling member 311 and a chest wall of the breast 1 becomes large. Therefore, it is likely that information on a portion in the vicinity of the chest wall of the breast 1 is not obtained, and accordingly, a position of detection of the bed 110 by the contacting sensor 330 is preferably set such that the bed 110 and the cup 310 are close to each other. The detection of a distance to the bed 110 is not limited to the detection using the contacting sensor 330, and an optical contacted sensor or a magnetic contacted sensor may be used. Alternatively, an encoder which detects a position of the maintaining unit 300 in the Z direction may be provided so that feedback control is performed. Furthermore, the driving of the X adjustment stage 510 and the Y adjustment stage 520 may be controlled by the calculation unit 400 using a motor. Alternatively, a controller for the X adjustment stage 510 and the Y adjustment stage 520 may be provided, and when a button representing a direction in which a certain one of the X adjustment stage 510 and the Y adjustment stage 520 is to be moved is pressed, the one of the X adjustment stage 510 and the Y adjustment stage 520 continues to be moved while the button is pressed.

Figure 4A:
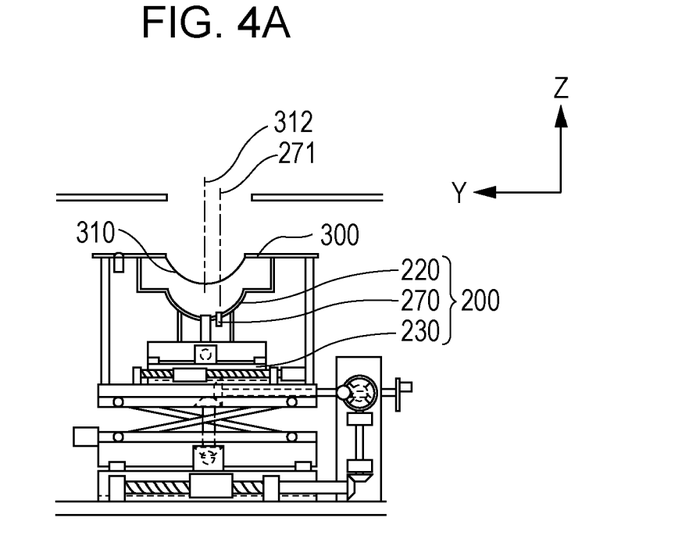
FIGS. 4A and 4B are diagrams illustrating positioning between a camera and a cup-shaped container according to the first embodiment.
Figure 4B:
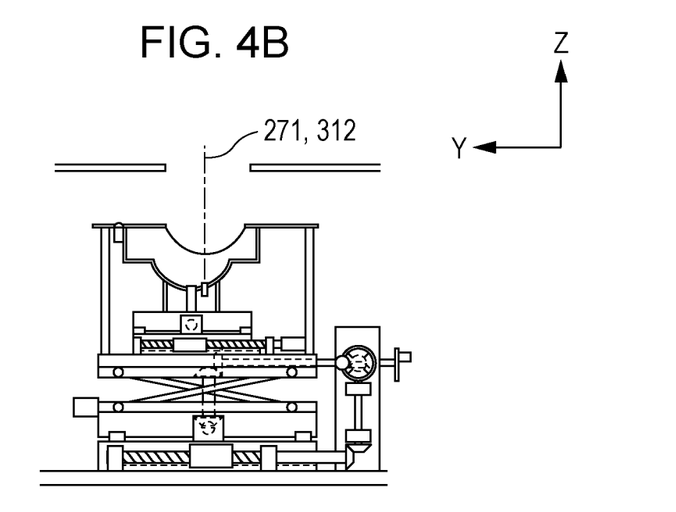

In this embodiment, a camera 270 is included in the ultrasonic wave detector 220 as an examination portion detection unit which detects the breast 1 which is the portion to be examined. The camera 270 is disposed such that an image of the breast 1 (more specifically, a nipple which will be described hereinafter) is captured from a lower portion of the ultrasonic wave detector 220. An optical axis 271 (refer to FIG. 4) of the camera 270 is directed to the Z direction and the camera 270 captures an image of the breast 1 through the cup 310. The image captured by the camera 270 is displayed in a monitor, not illustrated, in real time so that the operator may recognize the image. The camera 270 is preferably positioned such that the ultrasonic wave detector 220 is located in an image capturing initial position when a center axis 312 of the cup 310 and the optical axis 271 of the camera 270 coincide with each other so that a period of time before the image capturing is started is reduced. Here, the center axis 312 of the cup 310 is the center axis of a shape of the cup 310 in the Z direction, and when the cup 310 has a hemispherical shape, the center axis 312 corresponds to an axis in the Z direction which passes a center of curvature. Furthermore, a direction of the optical axis 271 of the camera 270 is not limited to the Z direction, and may be any direction as long as positioning between the breast 1 and the cup 310 is achieved. Furthermore, a plurality of directions may be set.

Next, the positioning between the breast 1 and the cup 310 will be described.

FIGS. 4A and 4B are diagrams illustrating matching of the axes of the camera 270 and the cup 310. Before the breast 1 is inserted, matching between the optical axis 271 of the camera 270 and the center axis 312 of the cup 310 is executed. As illustrated in FIG. 4A, when the optical axis 271 of the camera 270 and the center axis 312 of the cup 310 are shifted from each other, the scanning stage 230 is driven so that the optical axis 271 and the center axis 312 match each other as illustrated in FIG. 4B. In this embodiment, the measurement unit 200 and the maintaining unit 300 are integrated with each other as described above. Specifically, a position of the ultrasonic wave detector 220 relative to the measurement unit 200 and a position of the cup 310 disposed on in the maintaining unit 300 may be detected by an origin sensor and a linear encoder included in the scanning stage 230.

Figure 5A:
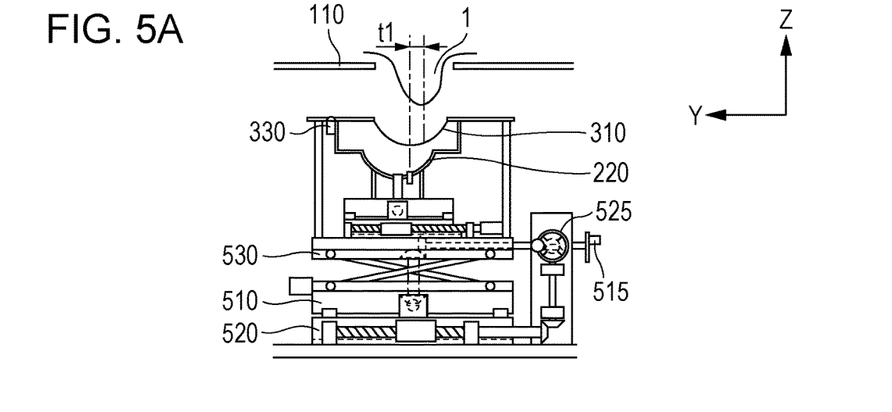
FIGS. 5A to 5C are diagrams illustrating positioning between a breast and the cup-shaped container according to the first embodiment.
Figure 5B:
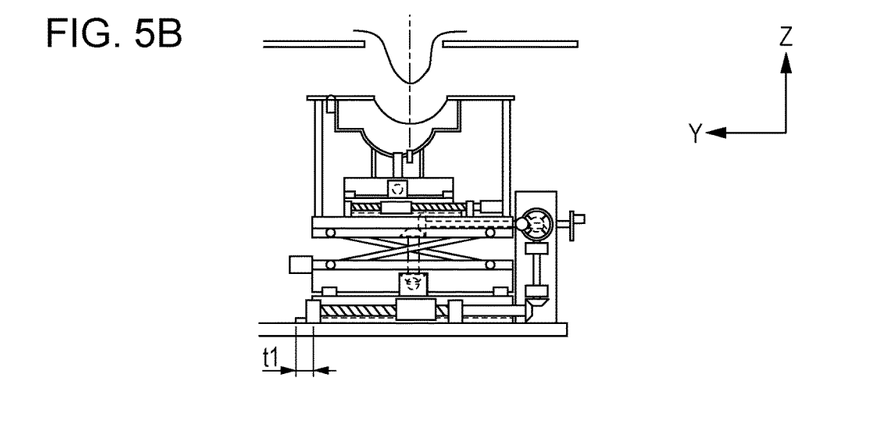
Figure 5C:
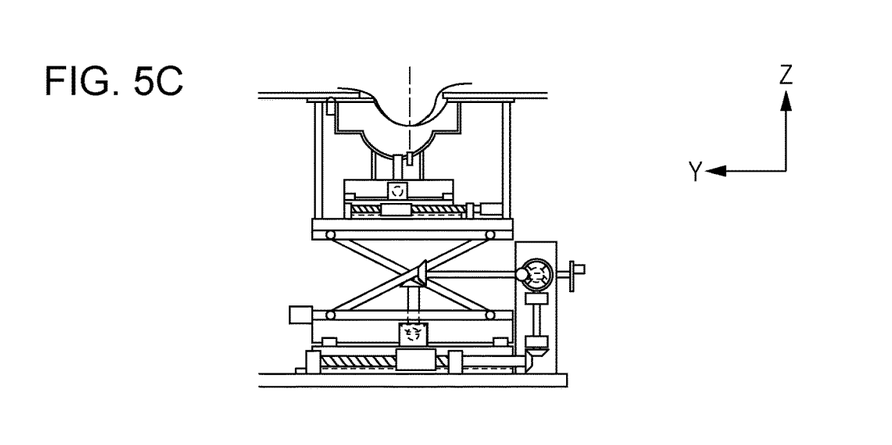
Figure 6A:
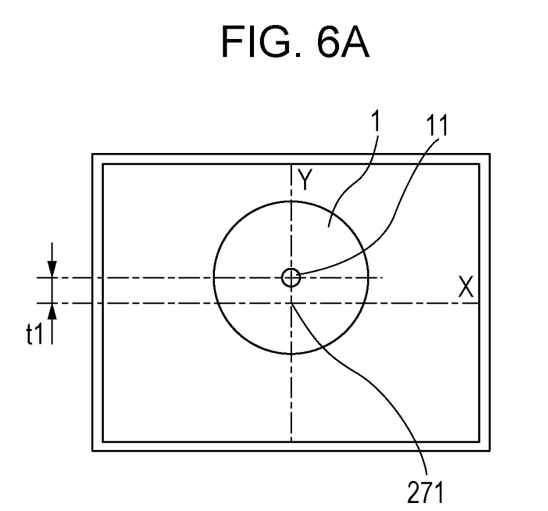
FIGS. 6A and 6B are diagrams illustrating camera images according to the first embodiment.
Figure 6B:
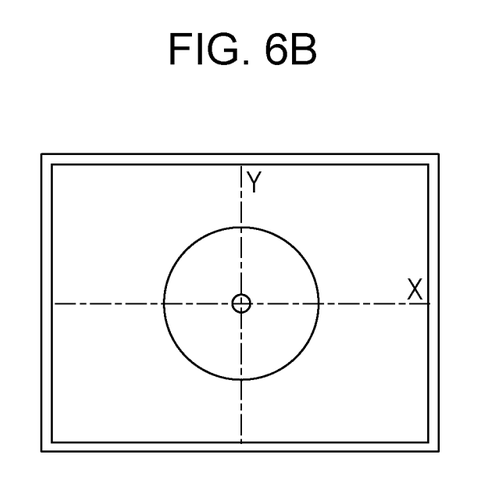

FIGS. 5A to 5C are diagrams illustrating the positional relationship between the breast 1 and the cup 310. FIG. 5A is a diagram illustrating the positional relationship obtained when the examinee lies on the bed 110 in a prone posture and inserts the breast 1 in the opening 111. FIG. 5B is a diagram illustrating the positional relationship obtained when the positioning between the breast 1 and the cup 310 is performed using the Y adjustment stage 520. FIG. 5C is a diagram illustrating the positional relationship obtained when the cup 310 is pressed against the breast 1 using the Z adjustment stage 530. In FIG. 5A, a position of the cup 310 is controlled such that the cup 310 is not in contact with the breast 1 when the examinee lies on the bed 110 in a prone posture and the breast 1 is inserted into the opening 111 of the bed 110 to sag. Furthermore, an amount of shift between the breast 1 and the cup 310 in the Y direction is denoted by t1. FIGS. 6A and 6B are diagrams illustrating images captured by the camera 270 which are displayed in the monitor. FIG. 6A is a diagram illustrating an image captured by the camera 270 in the state of FIG. 5A. FIG. 6B is a diagram illustrating an image captured by the camera 270 in the state of FIG. 5B. In this embodiment, a nipple 11 is set as an index of the positioning. A position of a center of the monitor corresponds to the optical axis 271 of the camera 270.

The operator operates the handle 525 while checking the positional relationship between the optical axis 271 of the camera 270 and the nipple 11 so as to move the Y adjustment stage 520 so that the positioning between the nipple 11 and the optical axis 271 of the camera 270 is performed as illustrated in FIG. 6B. Although only the Y direction is described here, positioning in the X direction may be performed using the X adjustment stage 510, and positioning is similarly performed on all directions in which a shift occurs. Since the optical axis 271 of the camera 270 matches the center axis 312 of the cup 310 as described above, the positioning between the breast 1 and the cup 310 may be performed. Although the nipple 11 is used as the index of the positioning of the breast 1 here, a mark is made on the breast 1 and the mark may be used as an index. Furthermore, the X adjustment stage 510 and the Y adjustment stage 520 may be driven by motors, and the calculation unit 400 may automatically perform positioning between the breast 1 and the cup 310 from the image illustrated in FIG. 6A (an output of the camera 270) using a general image recognition technique.

After the positioning between the breast 1 and the cup 310 is completed in the X and Y directions, driving of the Z adjustment stage 530 is started through the calculation unit 400. The maintaining unit 300 moves toward the bed 110, and the cup 310 is pressed against the breast 1. When the contacting sensor 330 included in the maintaining unit 300 detects the bed 110, the driving of the Z adjustment stage 530 is stopped and a state illustrated in FIG. 5C is realized. By the operation described above, supporting of the breast 1 before the measurement is completed and the measurement becomes available.

With this configuration, since the cup 310 may be moved such that the breast 1 is accommodated in a desired position, the positioning between the breast 1 and the cup 310 is performed with high accuracy without a burden of the examinee.

In the configuration described above, the Z adjustment stage 530 continues driving after the driving is started until the contacting sensor 330 detects the bed 110. However, the Z adjustment stage 530 may be stopped before the contacting sensor 330 detects the bed 110. In this case, when the cup 310 is in contact with the breast 1, Z adjustment is temporarily stopped and positions in the X and Y directions are checked and adjusted so that the positioning is performed with higher accuracy.

Note that, although a configuration in which the adjustment stage 500 is disposed below the measurement unit 200 and the measurement unit 200 and the maintaining unit 300 are movable relative to the bed 110 is employed, a configuration in which the bed 110 is movable relative to the measurement unit 200 and the maintaining unit 300 may be employed.

Second Embodiment

Figure 7:
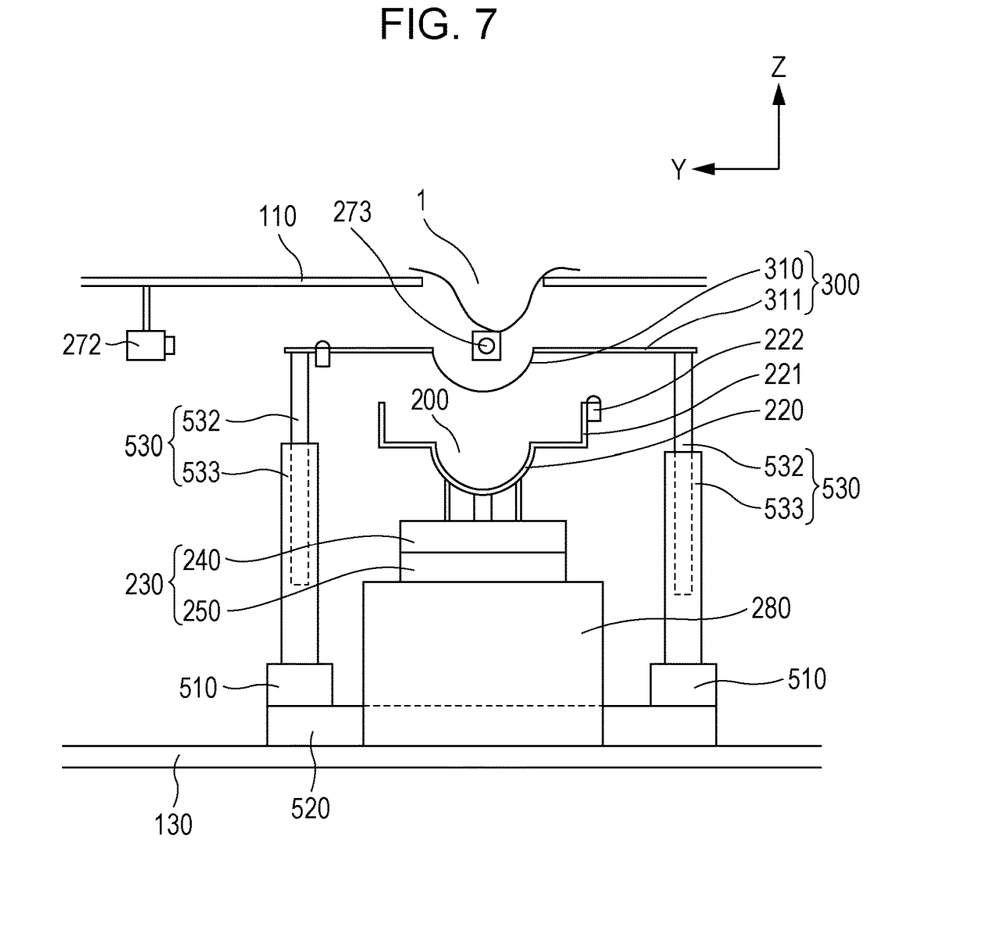
FIG. 7 is a side view illustrating an internal configuration of an examination portion information obtaining apparatus according to a second embodiment.

In a second embodiment, a maintaining unit 300 and a measurement unit 200 are movable relative to each other, and accordingly, only the maintaining unit 300 may be movable relative to a bed 110. Detailed descriptions of components having configurations the same as those of the first embodiment are omitted. FIG. 7 is a side view illustrating an internal configuration of an examination portion information obtaining apparatus according to the second embodiment. The measurement unit 200 includes a Y scanning stage 250, an X scanning stage 240, and an ultrasonic wave detector 220 disposed on a base 130 through a Z stage 280. A matching container 221 includes a maintaining unit detection sensor 222 which is a contacting type sensor and which detects the maintaining unit 300 on an outer surface thereof. The maintaining unit 300 includes a Y adjustment stage 520, an X adjustment stage 510, and a Z adjustment stage 530 disposed on the base 130 such that the Y adjustment stage 520, the X adjustment stage 510, and the Z adjustment stage 530 surround the measurement unit 200. A scanning stage 230 which moves the measurement unit 200 and an adjustment stage including the X adjustment stage 510, the Y adjustment stage 520, and the Z adjustment stage 530 which moves the maintaining unit 300 are independent from each other, and therefore, the measurement unit 200 and the maintaining unit 300 are movable relative to each other. The X adjustment stage 510 and the Y adjustment stage 520 have respective absolute encoders, not illustrated. Accordingly, a position of the maintaining unit 300 relative to the base 130 may be detected. The Z adjustment stage 530 slides using a shaft 532 and a guide 533 having a hole which fits the shaft 532. The X adjustment stage 510, the Y adjustment stage 520, and the Z adjustment stage 530 are driven by motors, not illustrated. Cameras which detect positions of a breast 1 and a cup 310 are disposed on the bed 110 near the maintaining unit 300. The cameras includes a Y-direction camera 273 which performs image capturing in an X direction and detects positions of the breast 1 and the cup 310 in the Y direction and an X-direction camera 272 which performs image capturing in a Y direction and detects the positions in the X direction.

Figure 8A:
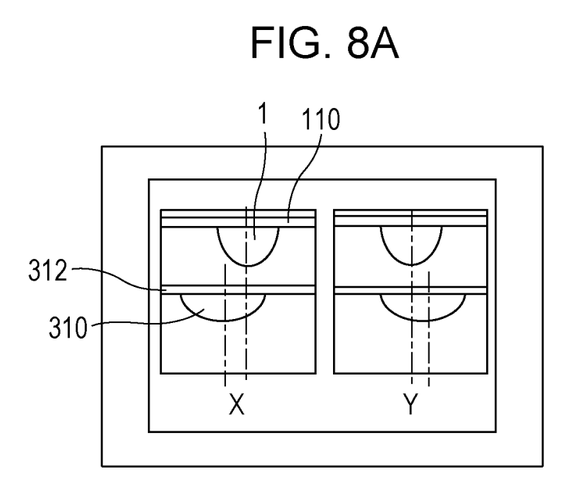
FIGS. 8A and 8B are diagrams illustrating camera images according to the second embodiment.
Figure 8B:
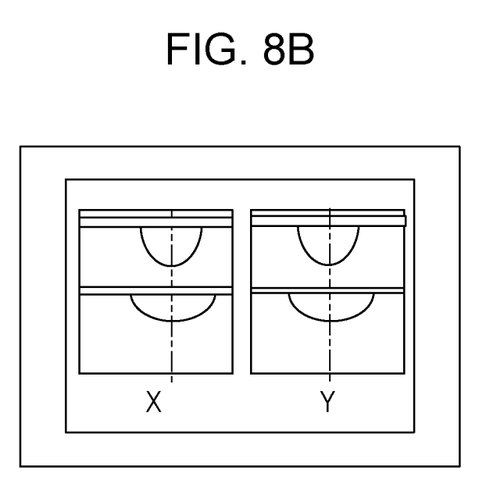
Figure 9A:
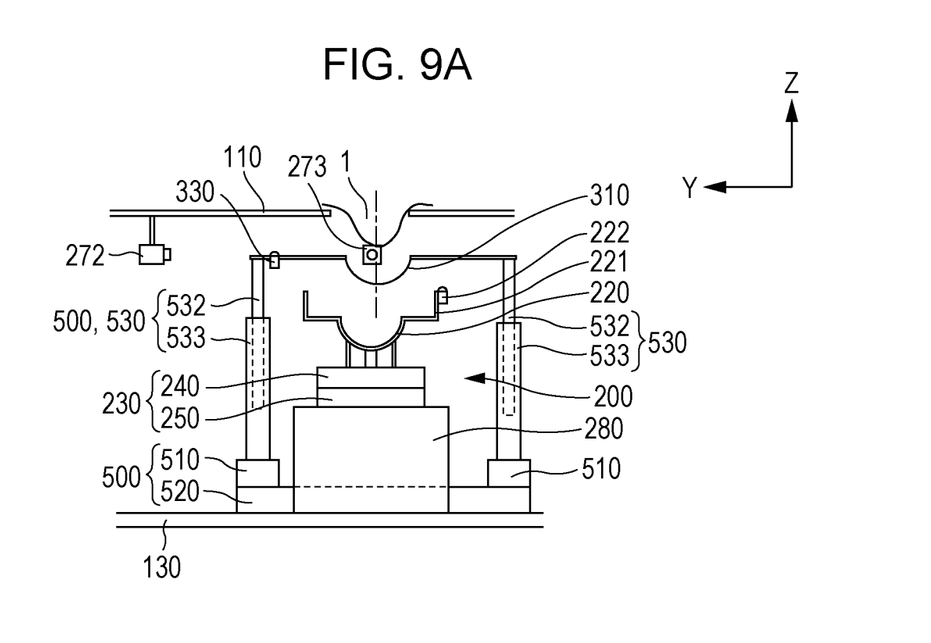
FIGS. 9A and 9B are diagrams illustrating positioning between a breast and a cup-shaped container according to the second embodiment.
Figure 9B:
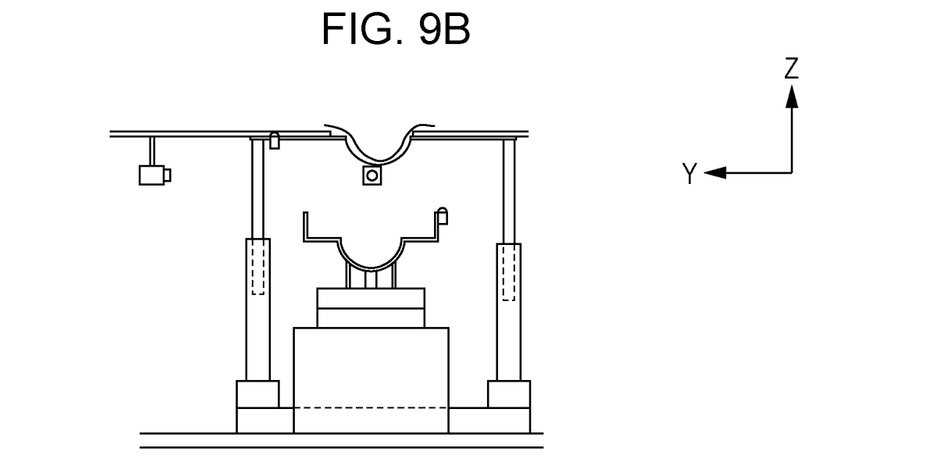

FIGS. 8A and 8B are diagrams illustrating images captured by the camera and displayed in a monitor. FIG. 8A is a diagram of an image obtained when the examinee inserts the breast 1 in an opening. FIG. 8B is a diagram of an image obtained after the positioning between the breast 1 and the cup 310 is performed. In an image of the X-direction camera 272, the sagging breast 1 which is inserted into the opening of the bed 110, the cup 310, and a cup assembling member 311 for the cup 310 are displayed. The same components are displayed in the image of the Y-direction camera 273. The operator performs positioning of the maintaining unit 300 using the monitor images. The operator operates the X adjustment stage 510 and the Y adjustment stage 520 such that an approximate center of the breast 1 and an approximate center of the cup 310 match each other. The operation is controlled through a calculation unit. As an operation method, the operator may perform operation using a controller, or the operator may perform operation of start of the adjustment and operation after the start of the adjustment may be automatically performed by image processing. Furthermore, as with the first embodiment, a nipple may be set as an index of the positioning of the breast 1, or a mark for the positioning may be set to the breast 1. FIG. 9A is a diagram illustrating an internal configuration after the positioning between the cup 310 and the breast 1 is completed by the operation described above. After the positioning in the X and Y directions of the cup 310 is completed, a contacting sensor 330 disposed on the maintaining unit 300 is moved in the Z direction to a position where the bed 110 is to be detected and the breast 1 is supported by the cup 310. FIG. 9B is a diagram illustrating an internal configuration when the support of the breast 1 by the cup 310 is completed.

A position of the cup 310 relative to the base 130 after the positioning may be detected by encoders, not illustrated, disposed on the X adjustment stage 510 and the Y adjustment stage 520. The ultrasonic wave detector 220 may be moved to a measurement start position in accordance with information on the position of the cup 310 detected by the encoders. Furthermore, the scanning stage 230 which causes the ultrasonic wave detector 220 to perform scanning may be moved in an expected movement range for the positioning of the cup 310 and a movement range required for measurement.

Figure 10A:
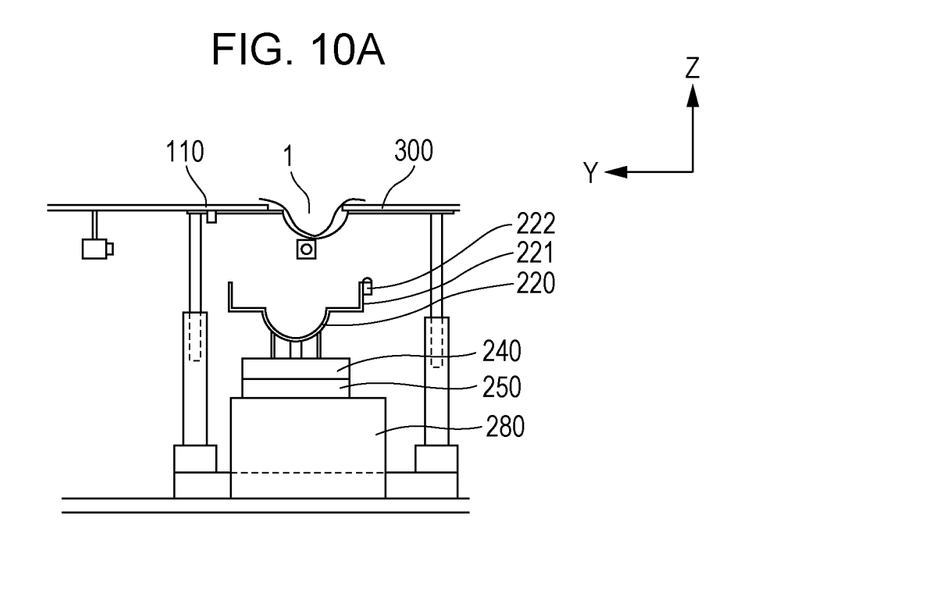
FIGS. 10A and 10B are diagrams illustrating positioning of an acoustic wave detector relative to the cup-shaped container according to the second embodiment.
Figure 10B:
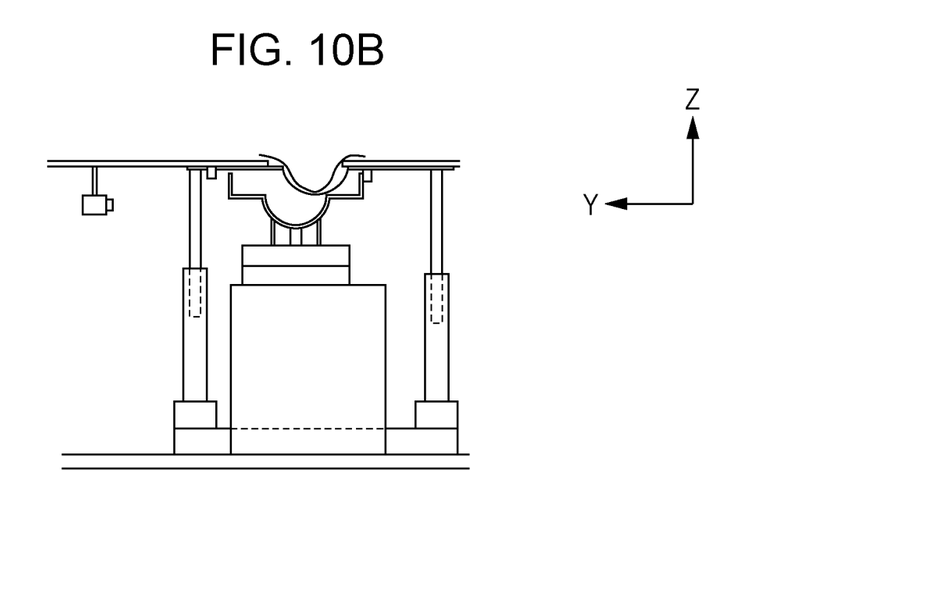

FIG. 10A is a diagram illustrating an internal configuration obtained when the support of the breast 1 by the cup 310 is completed, and furthermore, movement in the X and Y directions of the ultrasonic wave detector 220 to the measurement start position is completed. Thereafter, the Z stage 280 is driven to move the ultrasonic wave detector 220 toward the maintaining unit 300. FIG. 10B is a diagram illustrating an internal configuration after the ultrasonic wave detector 220 moves in the Z direction. The movement in the Z direction of the ultrasonic wave detector 220 is stopped when the ultrasonic wave detector 220 arrives at a position where the maintaining unit detection sensor 222 detects the maintaining unit 300. The movement in the Z direction of the ultrasonic wave detector 220 may be performed by another method such as a method for controlling a shift amount using an encoder disposed on the Z stage 280 or a method for controlling a shift amount by the number of pulses using a pulse motor for driving.

Although the X-direction camera 272 and the Y-direction camera 273 are used when the positioning between the breast 1 and the cup 310 is performed, positions of cameras and the number of cameras are not limited to this embodiment. Furthermore, instead of the camera, a sensor which detects an object may be used to detect a position of the breast 1 so that the positioning is performed.

The scanning stage 230 of the ultrasonic wave detector 220 has a scanning range corresponding to a region required for the measurement, and the cup 310 may be moved by a stage disposed below the measurement unit 200 for the positioning.

In the state in which the maintaining unit 300 and the measurement unit 200 are integrated with each other as illustrated in the first embodiment, the cup 310 is covered by the ultrasonic wave detector 220, and therefore, the cup 310 is not visually recognized. However, with the configuration of this embodiment, the cup 310 is separated from the ultrasonic wave detector 220, and therefore, the operator may visually recognize the cup 310. Accordingly, the positioning between the breast 1 and the cup 310 may be visually performed by the operator without the camera.

According to the configuration described above, the cup 310 may be moved so that the breast 1 is accommodated in a desired position, and accordingly, the positioning between the breast 1 and the cup 310 may be accurately performed without movement of an examinee. Furthermore, in this embodiment, since the cup 310 and the ultrasonic wave detector 220 may be moved relative to each other and are separated from each other, the positional relationship between the cup 310 and the breast 1 may be checked with ease when the positioning of the cup 310 relative to the breast 1 is performed.

In the second embodiment, the adjustment stage of the maintaining unit 300 is disposed on the base 130 as a configuration capable of moving the maintaining unit 300 and the measurement unit 200 relative to each other. However, the adjustment stage may be disposed on the bed 110. Next, modifications of the arrangement of the adjustment stage will be described.

Figure 11A:
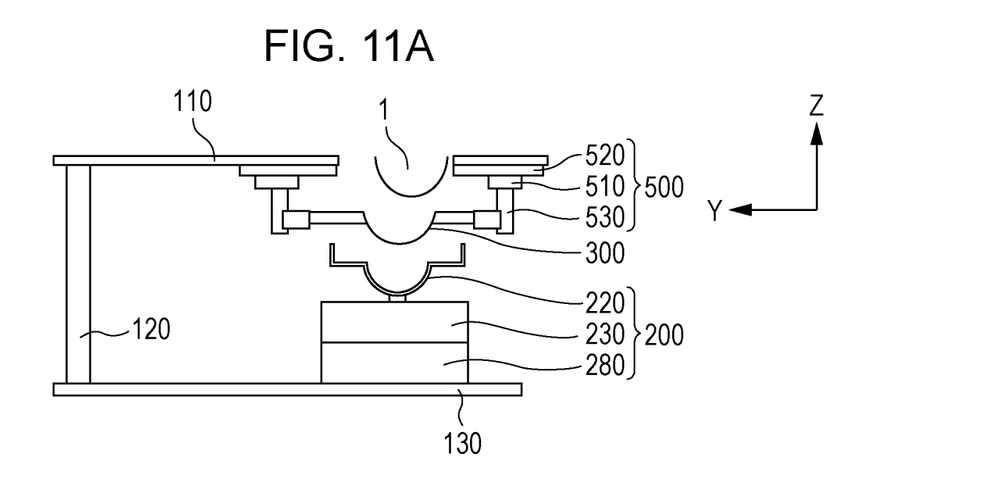
FIGS. 11A and 11B are diagrams illustrating modifications of a maintaining unit.
Figure 11B:
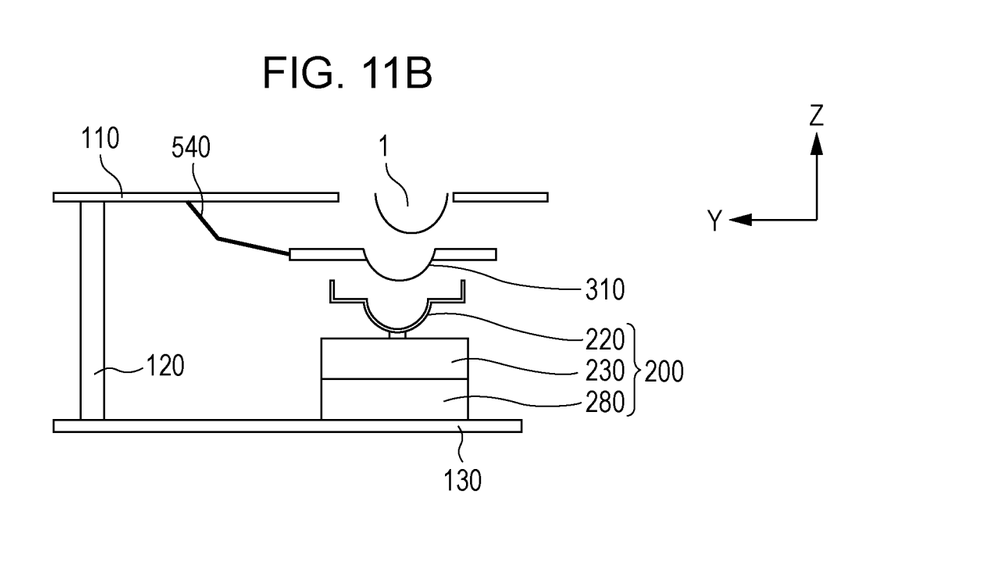

FIGS. 11A and 11B are diagrams simply illustrating a configuration of an inside of an apparatus when an X adjustment stage 510, a Y adjustment stage 520, and a Z adjustment stage 530 of a maintaining unit 300 are disposed on a bed 110. FIG. 11A is a diagram illustrating a state in which the maintaining unit 300 is disposed on the bed 110 to be movable relative to a measurement unit 200 and the bed 110 through the X adjustment stage 510, the Y adjustment stage 520, and the Z adjustment stage 530. Methods for driving the X adjustment stage 510, the Y adjustment stage 520, and the Z adjustment stage 530 are the same as those of the foregoing embodiment. The X adjustment stage 510, the Y adjustment stage 520, and the Z adjustment stage 530 have respective linear encoders. Since the bed 110 and a base 130 are integrally configured through a bed leg 120, detection of a position of the maintaining unit 300 relative to the base 130 may be performed also in this example. Accordingly, the positioning of a cup 310 relative to a breast 1 is performed, and an ultrasonic wave detector 220 may be moved to a detected position of the cup 310. FIG. 11B is a diagram illustrating a configuration in which the maintaining unit 300 is supported using an arm 540 extending from the bed 110. An angle sensor is disposed on a joint portion of the arm 540, and the angle sensor may detect a position of the cup 310 using an angle. The maintaining unit 300 may be driven by a handle operation instead of a motor. Alternatively, the maintaining unit 300 may be freely moved by a hand.

Also in this example, the ultrasonic wave detector 220 may be moved after a position of the cup 310 is detected. As described in the modifications above, even when the maintaining unit 300 is disposed on the bed 110, the cup 310 may be moved such that the breast 1 is accommodated in a desired position, and accordingly, positioning between the breast 1 and the cup 310 may be performed with high accuracy without movement of the examinee.

According to the present invention, positioning between a portion to be examined such as a breast and a cup-shaped maintaining member may be accurately performed without movement of an examinee. Consequently, a burden of the examinee may be reduced and a highly-reliable image may be obtained.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-227238 filed Oct. 31, 2013, which is hereby incorporated by reference herein in its entirety.

What is claimed is:

1. An examination portion information obtaining apparatus comprising:
   a bed member configured to support an examinee and having an opening through which a portion to be examined of the examinee is to be inserted;

a supporting member configured to support at least part of a portion to be examined of the examinee inserted through the opening and to be coupled with the bed member in a translationally movable manner with respect to the bed member;

an adjustment mechanism configured to move the supporting member horizontally with respect to the bed member so as to adjust a position of the supporting member with respect to the portion horizontally, while the supporting member is spaced apart from the portion;

a measuring member configured to measure information in the portion, the measuring member comprising:

an acoustic wave detector configured to receive acoustic waves from the portion, when the portion is irradiated with light from a light irradiation unit; and a scanning mechanism configured to cause the acoustic wave detector to move translationally with respect to the supporting member;

wherein the adjustment mechanism is configured to close the supporting member to the portion vertically after a horizontal adjustment by the adjustment mechanism.

2. The examination portion information obtaining apparatus according to claim 1, wherein
the adjustment mechanism is movable in a plane which is perpendicular to a direction in which the portion to be examined is inserted.

3. The examination portion information obtaining apparatus according to claim 1, wherein
the acoustic wave detector has a hemispherical shape, an approximate hemispherical shape, or a shape of 1/n of a spherical shape, and has an inner surface having a plurality of detection elements disposed in a spiral manner.

4. The examination portion information obtaining apparatus according to claim 1, further comprising:
a base on which the adjustment mechanism is mounted.

5. The examination portion information obtaining apparatus according to claim 1, further comprising:
a measurement unit base on which the supporting member and the acoustic wave detector are mounted,
wherein the supporting member is fixed to the measurement unit base, and
the adjustment mechanism moves the measurement unit base.

6. The examination portion information obtaining apparatus according to claim 1, wherein
the adjustment mechanism moves the supporting member in a direction in which the supporting member separates from the portion to be examined in a direction in which the portion to be examined is inserted before the adjustment of the supporting member is performed in a plane which is perpendicular to the direction in which the portion to be examined is inserted.

7. The examination portion information obtaining apparatus according to claim 1, further comprising:
a control unit configured to control the adjustment mechanism such that positioning between the supporting member and the portion to be examined is performed in accordance with an output from the detection unit which detects the relative position.

8. The examination portion information obtaining apparatus according to claim 1, wherein
the detection unit which detects the relative position is a camera.

9. The examination portion information obtaining apparatus according to claim 1, further comprising:

a second adjustment mechanism configured to move the acoustic wave detector relative to the supporting member.

10. The examination portion information obtaining apparatus according to claim 9, wherein
the second adjustment mechanism moves the acoustic wave detector in a direction in which the portion to be examined is inserted and in a plane which is perpendicular to that direction.

11. The examination portion information obtaining apparatus according to claim 9, wherein
the second adjustment mechanism which moves the acoustic wave detector moves the supporting member in a direction in which the supporting member separates from the portion to be examined in a direction in which the portion to be examined is inserted before the supporting member is moved in a plane which is perpendicular to the direction in which the portion to be examined is inserted.

12. The examination portion information obtaining apparatus according to claim 1, wherein
the acoustic wave detector includes a light irradiation unit, and
the acoustic waves are photoacoustic waves generated by light irradiation to the portion to be examined from the light irradiation unit.

13. The examination portion information obtaining apparatus according to claim 1, wherein
the supporting member is configured to be cup-shaped.

14. The examination portion information obtaining apparatus according to claim 1, wherein
the supporting member is configured to be changeable shape.

15. The examination portion information obtaining apparatus according to claim 1, wherein
the portion is a part of the examinee in a prone posture on the bed member.

16. An examination portion information obtaining apparatus comprising:
a bed member configured to have an opening through which a portion to be examined of an examinee is to be inserted;
a supporting member configured to accommodate at least part of the portion to be examined inserted into the opening and to be coupled with the bed member in a translationally movable manner with respect to the bed member;
an acoustic wave detector configured to receive acoustic waves from the portion to be examined; and
an adjustment mechanism configured to move the supporting member horizontally with respect to the bed member and adjust a position of the supporting member with respect to the portion, while the supporting member is spaced apart from the portion,
wherein the adjustment mechanism is configured to elevate the supporting member to the portion vertically after a horizontal adjustment by the adjustment mechanism.

17. The examination portion information obtaining apparatus according to claim 16, wherein
the adjustment mechanism moves the bed member and the supporting member relative to each other in a direction in which the portion to be examined is inserted.

18. The examination portion information obtaining apparatus according to claim 16, further comprising:

a scanning mechanism configured to cause the acoustic wave detector to move translationally with respect to the supporting member.

\* \* \* \* \*